United States Patent [19]

Vanderheyden et al.

[11] Patent Number: 4,990,787

[45] Date of Patent: Feb. 5, 1991

[54] RADIONUCLIDE GENERATOR SYSTEM AND METHOD FOR ITS PREPARATION AND USE

[75] Inventors: Jean-Luc Vanderheyden; Fu-Min Su, both of Seattle, Wash.

[73] Assignee: NeoRx Corporation, Seattle, Wash.

[21] Appl. No.: 416,221

[22] Filed: Sep. 29, 1989

[51] Int. Cl.$^5$ ............................................... C01G 47/00
[52] U.S. Cl. ............................................... 250/432 PD
[58] Field of Search ................................. 250/432 PD

[56] References Cited

U.S. PATENT DOCUMENTS

| | | | |
|---|---|---|---|
| 4,123,497 | 10/1978 | Ruddock | 423/49 |
| 4,280,053 | 7/1981 | Evans et al. | 250/432 PD |
| 4,859,431 | 8/1989 | Ehrhardt | 250/432 PD |

FOREIGN PATENT DOCUMENTS 2160010  12/1985  United Kingdom ......... 250/432 PD

*Primary Examiner*—Bruce C. Anderson
*Attorney, Agent, or Firm*—Christensen, O'Connor, Johnson & Kindness

[57] ABSTRACT

Improved radionuclide generators include a substantially insoluble salt of a parent radionuclide precursor which may be directly irradiated and then packed in a column for subsequent elution of the daughter radionuclide without the production of counter ion isotopic contaminants. The parent radionuclide precursor is provided in the form of an insoluble salt of the parent element whose counter ion, preferably aluminum, forms a relatively soluble salt with the desired daughter radionuclide. The improved generators may be prepared by reacting a parent radionuclide precursor with aluminum to obtain an aluminum salt of the precursor having low solubility in water, irradiating the aluminum salt to obtain an irradiated aluminum salt of the parent radionuclide, and then disposing the irradiated parent radionuclide in an elutable container. Useful parent radionuclide precursors include molybdenum-98 in the form of molybdate for the production of daughter $^{99m}$Tc, as soluble pertechnetate, and tungsten-186 in the form of tungstate for the production of daughter $^{188}$Re as soluble perrhenate. The daughter $^{99m}$Tc or $^{188}$Re may be eluting the generator matrix, e.g., with a saline solution.

11 Claims, No Drawings

RADIONUCLIDE GENERATOR SYSTEM AND METHOD FOR ITS PREPARATION AND USE

FIELD OF THE INVENTION

This invention relates to the production of radionuclides useful for therapeutic and diagnostic medical applications. More particularly, the invention relates to radionuclide generator systems, such as rhenium-188 generators and technetium-99m generators.

BACKGROUND OF THE INVENTION

Some radionuclides, atomic species that may exhibit radioactivity, are useful for diagnostic and therapeutic techniques such as tumor imaging and radiotherapy of tumors. The adoption and expanded use of these techniques has increased the demand for available supplies of carrier-free radionuclides having useful half-lives and suitable gamma and/or beta emission properties. Two radionuclides which have received particular attention for these purposes are technetium-99m ($^{99m}$Tc, half-life 6.02 hours) used for diagnostic purposes and rhenium-188 ($^{188}$Re, half-life 16.98 hours) used for therapeutic and diagnostic purposes.

Technetium-99m ($^{99m}$Tc) has been widely studied and used in diagnostic nuclear medicine since the later 1950s. $^{99m}$Tc produces a readily imageable gamma emission (140 kev, 90%) which facilitates monitoring of its biodistribution when injected in vivo after conjugation or complex formation with other compounds, such as target-specific antibodies. The chemistry of technetium has been well developed, primarily through study of the relatively stable isotope technetium-99 ($^{99}$Tc, half-life 210,000 years).

Although the chemical properties of rhenium are not as well known as those of technetium, certain isotopes of rhenium exhibit properties that indicate it is suited for both radiodiagnostic and radiotherapeutic applications, for example, as a label for conjugation to monoclonal antibodies for targeting to tumors. $^{188}$Re (half-life 16.98 hours) has a longer half-life than $^{99m}$Tc (6.02 hours), possesses a strong particulate emission (beta energy of 2.12 MeV, as compared with $^{99m}$Tc which has no particulate emission), and has an imageable gamma emission (15%, 155 kev) suitable for gamma camera imaging of tumors. $^{188}$Re is derived from either natural rhenium-187 ($^{187}$Re) by neutron bombardment in a nuclear reactor or, preferably, from a $^{188}$W/$^{188}$Re generator made of a target tungsten material, enriched in W-186, by double neutron capture using a high-flux reactor. The nuclear properties of this isotopic system are as follows:

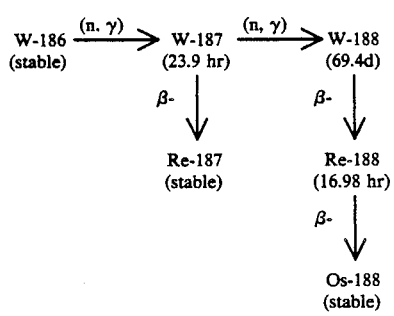

One method of producing $^{99m}$Tc and $^{188}$Re involves extraction of a relatively short-lived "daughter" radionuclide as a decay product of a longer lived ("parent") radionuclide. For example, $^{99m}$Tc is the daughter radionuclide of molybdenum-99 ($^{99}$Mo, half-life 66.02 hrs) and $^{188}$Re is the daughter of tungsten-188 ($^{188}$W, half-life 69.4 days). Devices known as generators have been commercially available to provide the parent radionuclide in convenient, ready-to-use form and to provide for separation of the daughter radionuclide from its parent radionuclide to obtain a supply of the relatively short-lived daughter isotope. The parent and daughter radionuclides may be separated using chromatographic, solvent extraction, or sublimation generators. Chromatographic generators, due to their simplicity and compact nature, are more convenient to use in hospitals and other institutions where radionuclides are used for diagnosis and therapy. For use in such generators, the parent radionuclide must have a sufficiently long half-life to provide for transit and storage prior to commencing the extraction procedure.

In one form of chromatographic generator, such as those used to produce $^{99m}$Tc from $^{99}$Mo, insolubilized parent radionuclide is adsorbed onto a bed or column of material such as aluminum oxide ("alumina") for which the daughter radionuclide has relatively little affinity. The daughter radionuclide, which results from decay of the parent, is then periodically eluted from the column, for example, using physiological saline. Typically, the daughter radionuclide product will be of high specific activity and is referred to as "carrier free" since it is produced by beta decay of a parent radionuclide, and the product is relatively free of stable isotopes of the daughter radionuclide.

Although adsorption column chromatographic generators are capable of producing daughter radionuclides, chromatographic generators of this type are only able to provide high specific activity daughter radionuclides at relatively low concentrations from low specific activity (n,γ) parent radionuclides, such as $^{99}$Mo and $^{188}$W, due to the necessity of using large quantities of alumina or other adsorption bed material and eluting solution to obtain the daughter radionuclide. As a result, fission- or high flux neutron capture-produced parent radionuclides were formely preferred for producing radionuclides such as $^{99m}$Tc and $^{188}$Re. Unfortunately, fission-produced radionuclides require complex facilities and safety precautions that entail high costs relative to the amount of daughter radionuclide produced. In addition, the relatively short half-lives of the desired radionuclides, $^{99m}$Tc and $^{188}$Re, preclude convenient production of fission- or neutron capture-produced radionuclides at an established nuclear reactor and subsequent shipment to a hospital or clinic for further preparation and use.

Recently, an alternative chromatographic $^{99}$Mo/$^{99m}$Tc generator was developed, as described in Evans et al., U.S. Pat. No. 4,280,053, in which the parent isotope, $^{99}$Mo, is formulated directly into the solid phase of the generator column in the form of insoluble zirconium molybdate. In order to produce the Evans et al. $^{99}$Mo/$^{99m}$Tc generator, molybdenum trioxide (enriched in $^{98}$Mo to produce $^{99}$Mo) is irradiated and then dissolved in a basic ammonia or sodium hydroxide solution. The resulting solution is acidified and added to an aqueous zirconium nitrate or zirconium chloride solution to obtain a zirconium molybdate precipitate in the form of a gel-like matrix. The matrix is then separated from the solution by filtration or evaporation, air dried and sized for use in the generator. The zirconium molybdate matrix is said to be non-elutable while allowing the daughter $^{99m}$Tc in the form of pertechnetate ion, $^{99m}$TcO$_4^-$, to freely diffuse from the matrix during elution. Since the parent $^{99}$Mo is incorporated directly into the gel, and is not retained by adsorption, the Evans et al. zirconium molybdate generator provides a significantly more dense $^{99}$Mo medium than prior alumina adsorption column generators.

More recently, U.S. Pat. No. 4,859,931, of Ehrhardt discloses an improved $^{188}$Re generator in which an insoluble zirconyl tungstate matrix containing $^{188}$W decays over time producing $^{188}$Re in the form of perrhenate ($^{188}$ReO$_4^-$), which is readily elutable from the matrix. The zirconyl tungstate matrix as disclosed in the Ehrhardt patent is produced by dissolving irradiated tungsten trioxide in a heated basic solution, adding the basic tungsten trioxide solution to an acidic zirconium-containing solution to obtain an acidic zirconyl tungstate slurry containing $^{188}$W, drying the slurry to form a permeable matrix, and then packing the matrix in an elutable column. The Ehrhardt generator has been found to be a highly effective generator of $^{188}$Re.

Although both the zirconyl molybdate generator system of Evans et al. and the zirconyl tungstate generator system of Enrhardt have proven to be effective for the production of $^{99m}$Tc and $^{188}$Re, respectively, these systems have inherent drawbacks which limit their large-scale use and acceptability. Both systems require significant handling and processing of irradiated materials, including dissolution, precipitation, filtration, drying, gel fragmentation and column packing steps, all occurring after irradiation of the molybdenum trioxide or tungsten trioxide starting materials. These processing steps with irradiated materials necessitate the use of cumbersome shielded processing equipment, result in relatively high manufacturing costs and pose significant potential safety risks.

In order to overcome some of the foregoing problems in connection with the production of $^{99m}$Tc, Narasimhan et al., "A New Method for $^{99m}$Tc Generator Preparation," *J. Radioanal. Nucl. Chem.*, Letters, Vol. 85, No. 6, pp. 345-356 discloses an improved method of preparing a zirconium molybdate $^{99m}$Tc generator in which the precipitation, filtration, drying and fragmentation of radioactive materials required in the preparation of zirconium molybdate $^{99m}$Tc generator are avoided by directly irradiating zirconium molybdate instead of molybdenum trioxide as disclosed by Evans. However, the direct irradiation of zirconium molybdate as reported by Narasimhan resulted in the production of radioactive contaminants unacceptable for clinical therapeutic or diagnostic applications, including $^{97}$Zr, $^{95}$Zr, $^{175}$Hf, $^{181}$Hf, and $^{24}$Na.

SUMMARY OF THE INVENTION

It has now been discovered that the foregoing problems associated with prior art zirconyl molybdate and zirconyl tungstate generator systems may be overcome through the use of improved radionuclide generators comprising a substantially insoluble salt of a parent radionuclide precursor which may be directly irradiated and then packed in a column for subsequent elution of the daughter radionuclide without the production of counter ion isotopic contaminants. The parent radionuclide precursor is provided in the form of an insoluble salt of the parent element whose counter ion forms a relatively soluble salt with the desired daughter radionuclide. Aluminum counter ions are presently preferred for this purpose. The improved generators of the invention may be prepared by reacting a parent radionuclide precursor with aluminum to obtain an aluminum salt of the precursor having low solubility in water, irradiating the aluminum salt to obtain an irradiated aluminum salt of the parent radionuclide, and then disposing the irradiated parent radionuclide in an elutable container. Useful parent radionuclide precursors include molybdenum-98 in the form of molybdate for the production of daughter $^{99m}$Tc, as soluble pertechnetate, and tungsten-186 in the form of tungstate for the production of daughter $^{188}$Re as soluble perrhenate. The daughter $^{99m}$Tc or $^{188}$Re may be recovered by eluting the generator matrix, e.g., with a saline solution. The eluant may be further purified, if desired, using a conventional alumina or zirconium oxide ion exchange medium.

DETAILED DESCRIPTION OF THE INVENTION

In accordance with the present invention, improved radionuclide generators for the production of $^{99m}$Tc or $^{188}$Re comprise a substantially insoluble salt of a radionuclide precursor disposed in an elutable container. Suitable radionuclide precursors comprise isotopes which, upon irradiation, form the desired parent radionuclides, i.e., $^{98}$Mo for use in a $^{99}$Mo/$^{99m}$Tc generator system, and $^{186}$W for use in a $^{188}$W/$^{188}$Re generator system. The radionuclide precursor is provided in the form of an insoluble salt of molybdate or tungstate having a counter ion which forms a relatively soluble salt with the desired daughter radionuclide, and which does not form undesirable contaminating isotopes upon irradiation. The presently most preferred counter ions for this purpose are aluminum cations. Thus, in one aspect of the invention, improved radionuclide generators are obtained by using aluminum molybdate comprising $^{98}$Mo or aluminum tungstate comprising $^{186}$W as irradiation targets, irradiating the aluminum salt of the parent radionuclide precursor to obtain an irradiated aluminum salt of the parent radionuclide, and then disposing the irradiated parent radionuclide in an elutable container. Production of the generators of the invention provides significant advantages over prior zirconyl molybdate and zirconyl tungstate gel matrix-type generator systems, since the insoluble aluminum salt of the parent radionuclide precursor may be directly irradiated and then packed into a column, thereby avoiding the cumbersome processing steps required in the production of the prior art zirconium generator systems.

After irradiation, the irradiated parent radionuclide, $^{99}$Mo or $^{188}$W, decays to form highly soluble daughter radionuclide ions, in the form of pertechnetate ($^{99m}$TcO$_4^-$), and perrhenate ($^{188}$ReO$_4^-$), respectively, which may be readily eluted from the column in aqueous form for direct use in medical diagnostic or therapeutic applications.

In the practice of the invention, aluminum molybdate or aluminum tungstate may be obtained by reacting enriched molybdenum trioxide ($^{98}$MoO$_3$) or tungsten trioxide ($^{186}$WO$_3$) with a strong base, such as sodium hydroxide or ammonium hydroxide, to obtain an aqueous molybdate or tungstate solution, and then adding a soluble salt of aluminum, such as aluminum chloride or aluminum nitrate, to the solution to yield the desired insoluble aluminum molybdate or aluminum tungstate. The substantially insoluble salts of the parent radionuclide precursor are irradiated at high neutron flux levels on the order of $10^{14}$ to $10^{15}$ neutrons/cm$^2$/sec using, for example, a 10 megawatt nuclear reactor to produce the irradiated parent radionuclide.

Irradiated parent radionuclide salts may be transferred to an empty container for eluting and harvesting of the daughter radionuclide products. Suitable containers may include, for example, a glass column such as those used in standard chromatography encased in a "shell" including appropriate lead shielding, associated plumbing and a reservoir of eluant to form a generator assembly. Alternatively, a separate sterile reservoir may be supplied for each series of elutions. It is desirable, but not essential, to keep the matrix hydrated at all times. Periodically, the daughter radionuclide is conveniently eluted from the column using a suitable eluant solution, such as water or saline. A presently particularly preferred eluant solution is physiological saline.

Performance of an improved generator of the present invention may be expressed as elution efficiency. Elution efficiency may be calculated by measuring the amount of radioactivity of the daughter radionuclide present in the eluant divided by the amount of radioactivity of the daughter radionuclide originally present on the generator column, immediately prior to elution. The radioactivity of the radionuclide may be determined using standard instruments for measuring radioactivity including gamma ray spectrophotometers such as germanium detectors and sodium iodide scintillation spectrophotometers, which are capable of measuring low levels of radioactivity, or dose calibrators that can measure high levels of radioactivity. In the present invention, since the generator consists of a small column, the entire column may be placed in a dose calibrator to directly measure the radioactivity of daughter radionuclide on the column before elution, and by subtracting from this value the amount of radioactivity of the daughter radionuclide on the column after elution, the amount of radioactivity of the radionuclide present in the eluant may be determined. This procedure provides a close approximation of the daughter radionuclide present in the eluant because, at the appropriate setting on the dose calibrator, the radioactivity measured on the column may be attributed to daughter radionuclide. Elution efficiencies are typically measured after approximately 3 to 10 daughter radionuclide half-lives.

The radiochemical purity of the daughter radionuclide may be assessed using ion exchange, reversed phase high-performance liquid chromatography (HPLC) or scintillator chromatography using nonradioactive perrhenate as a standard.

During the elution process, a certain amount of the parent radionuclide may be released onto the eluant, for example, in the form of small particles of the aluminum molybdate or aluminum tungstate, causing contamination of the daughter radionuclide. A porous glass or plastic structure, such as a fritted glass disc used in chromatography columns, may be used to retain some of these particles to prevent entry of tungsten into the eluate. Moreover, the level of parent radionuclide present in the eluant may be reduced by several orders of magnitude using a substrate which is capable of adsorbing the parent radionuclide, such as an alumina column or zirconium hydroxide bed, to purify the solution eluted from the generator. Thus, the generator system of the present invention may include a second elutable container, such as a chromatographic column enclosing a molybdenum- or tungsten-specific substrate, for removing any released $^{99}$Mo or $^{188}$W, in addition to the container enclosing the generator matrix. Alternatively, the substrate which is capable of adsorbing molybdenum or tungsten may be incorporated into the generator column, for example, below the aluminum molybdate or tungstate matrix, so that the eluant passes through the substrate after first flowing through the molybdate or tungstate matrix. An additional advantage of the use of the molybdate- or tungsten-adsorbing substrate is that the loss of small particles of matrix may be minimized, which in turn decreases the amount of eluted fluid containing such contamination particles which must be disposed of.

$^{99}$Mo/$^{99m}$Tc and $^{188}$W/$^{188}$Re generator devices made according to the present invention are quite compact and may be made using small masses of generator matrix. Since the $^{99}$Mo and $^{188}$W can be produced at a specific activity of approximately 1–100 Curie (Ci)/gram or higher by neutron capture, it is apparent that small (Curie size) generator columns containing volumes as low as 5 ml may be constructed using this process.

The foregoing may be better understood in connection with the following representative examples which are presented for purposes of illustration, not limitation, of the inventive concepts.

EXAMPLE 1

Synthesis of Al$_2$(WO$_4$)$_3$ from $^{186}$WO$_3$

To 400 mg(1.71 mmol) of enriched $^{186}$WO$_3$(96% $^{186}$W, Oak Ridge National Laboratory, Oak Ridge, Tenn.) in a 10 ml beaker was added 1 ml of 5N NaOH and 1 ml of D. I. water. The resulting mixture was heated to 70° C. and stirred for five minutes, until the solid was dissolved and a clear solution was obtained. The pH of the solution was then adjusted to 7.0±0.1 using a free electrode by the addition of 300 μl of conc. HCl, followed by the dropwise addition of 6N HCl. A light yellow tungstate solution was obtained after pH adjustment. During HCl addition, some yellow solid particles formed which dissolved after additional stirring.

In a separate container, 275 mg of AlCl$_3$.6H$_2$O (1.14 mol) was dissolved in 2.5 ml of D. I. water. The aluminum solution was added dropwisely into the tungsten solution. A shift to acidic pH was observed and little precipitate was formed after addition of the aluminum chloride solution. The pH of solution was adjusted to 4 with 1 N NaOH, yielding a bulky white aluminum tungstate precipitate. The solid was filtered by medium Buchner funnel, and washed by two times 25 ml of D. I. water. The solid was then heated in an oven at 105° C. for 2 hours. 400 mg of white solid was obtained (87% yield).

EXAMPLE 2

Preparation of $^{188}$Re Generator 400 mg of $^{186}$W enriched aluminum tungstate prepared according to the procedure of Example 1 was sealed in an irradiation container and subjected to neutron bombardment at a flux rate of 3×10$^{14}$ neutrons/cm$^2$/sec for 1 week at the Missouri University Research Reactor, Columbia, Missouri. Tungsten-187 (half-life, 24 hours) was allowed to decay from the irradiated material. Then, the irradiated aluminum tungstate was packed into a conventional generator column and eluted with 5 to 10 ml of physiological saline solution. 15% to 20% elution yields were obtained and eluated activity was identified as $^{188}ReO_4^-$ by both multichannel analyzer and RP-HPLC.

While the invention has been described in conjunction with certain presently preferred embodiments, various modifications and equivalents will be apparent to one of ordinary skill in the art after reading the foregoing specification. It is intended that any such modifications and equivalents be included in the scope of the appended claims except insofar as precluded by the prior art.

What is claimed is:

1. A method of preparing a generator for producing a daughter radionuclide from a parent radionuclide, comprising:
   irradiating an irradiation target comprising an insoluble aluminum salt of a precursor isotope of the parent radionculide at high neutron flux levels to obtain an irradiated aluminum salt of the parent radionuclide, and
   disposing the irradiated aluminum salt in an elutable container.

2. The method of claim 1 wherein the parent radionuclide precursor comprises an isotope selected from the group consisting of molybdenum-98 and tungsten-186.

3. The method of claim 2 wherein the parent radionuclide precursor comprises tungsten-186 in the form of aluminum tungstate.

4. The method of claim 2 wherein the parent radionuclide precursor comprises molybdenum-98 in the form of aluminum molybdate.

5. A radionuclide generator for producing a daughter radionuclide from a parent radionuclide comprising an insoluble, neutron-irradiated aluminum salt of the parent radionuclide disposed in an elutable container.

6. The generator of claim 5 wherein the aluminum salt comprises tungsten-188.

7. The generator of claim 5 wherein the aluminum salt comprises molybdenum-99.

8. The generator of claim 5 wherein the aluminum salt is selected from the group consisting of aluminum tungstate and aluminum molybdate.

9. A method of producing a daughter radionuclide from a parent/daughter radionuclide pair, comprising irradiating an insoluble aluminum salt of a precursor isotope of the parent radionuclide at high neutron flux levels, disposing the insoluble aluminum salt in an elutable container, and eluting the container to obtain the daughter radionuclide.

10. The method of claim 9 wherein the insoluble aluminum salt of the precursor isotope is aluminum tungstate comprising tungsten-186.

11. The method of claim 10 wherein the insoluble aluminum salt of the precursor isotope is aluminum molybdate comprising molybdenum-98.

* * * * *